(12) United States Patent
Sambusseti

(10) Patent No.: US 10,507,095 B2
(45) Date of Patent: Dec. 17, 2019

(54) RESORBABLE DEVICE FOR RECONSTRUCTING ROTATOR CUFFS

(71) Applicant: Antonio Sambusseti, Cremona (IT)

(72) Inventor: Antonio Sambusseti, Cremona (IT)

( * ) Notice: Subject to any disclaimer, the term of this patent is extended or adjusted under 35 U.S.C. 154(b) by 0 days.

(21) Appl. No.: 15/526,165

(22) PCT Filed: Nov. 12, 2015

(86) PCT No.: PCT/IB2015/058750
§ 371 (c)(1),
(2) Date: May 11, 2017

(87) PCT Pub. No.: WO2016/075652
PCT Pub. Date: May 19, 2016

(65) Prior Publication Data
US 2017/0340425 A1  Nov. 30, 2017

(30) Foreign Application Priority Data
Nov. 13, 2014  (IT) .............................. MI2014A1959

(51) Int. Cl.
*A61F 2/08* (2006.01)
*A61F 2/00* (2006.01)
*A61B 17/11* (2006.01)
*A61B 17/00* (2006.01)

(52) U.S. Cl.
CPC ........ *A61F 2/0063* (2013.01); *A61B 17/1146* (2013.01); *A61F 2/08* (2013.01); *A61B 2017/00004* (2013.01); *A61F 2002/0068* (2013.01); *A61F 2210/0004* (2013.01); *A61F 2230/0023* (2013.01)

(58) Field of Classification Search
CPC .. A61F 2/08; A61F 2/0063; A61F 2002/0068; A61F 2210/004; A61F 2230/0023; A61L 17/06; A61L 31/148; A61B 2017/00004
See application file for complete search history.

(56) References Cited

U.S. PATENT DOCUMENTS

| 4,149,277 | A | 4/1979 | Bokros |
| 5,084,151 | A | 1/1992 | Vallana et al. |
| 6,946,003 | B1 * | 9/2005 | Wolowacz ................ A61F 2/08 |
| | | | 623/23.72 |
| 2003/0212456 | A1 | 11/2003 | Lipchitz et al. |
| | | (Continued) | |

FOREIGN PATENT DOCUMENTS

| EP | 0744165 A1 | 11/1996 |
| EP | 1537883 A2 | 6/2005 |
| | (Continued) | |

OTHER PUBLICATIONS

International Search Report and Written Opinion dated Feb. 10, 2016 for PCT/IB2015/058750 to Antonio Sambusseti filed Nov. 12, 2015.

*Primary Examiner* — Brian A Dukert
(74) *Attorney, Agent, or Firm* — Vorys, Sater, Seymour and Pease LLP

(57) ABSTRACT

A device for the reconstruction of the rotator cuff including a flat element having at least two opposite ends and adapted to be connected to at least one of the damaged tendons of the rotator cuff of a patient at the ends; the flat element being entirely made of biodegradable and resorbable material.

15 Claims, 1 Drawing Sheet

(56) References Cited

U.S. PATENT DOCUMENTS

| | | |
|---|---|---|
| 2008/0319460 A1 | 12/2008 | Cortellini |
| 2010/0318108 A1 | 12/2010 | Datta et al. |
| 2011/0224702 A1* | 9/2011 | Van Kampen ............ A61F 2/08 606/151 |
| 2011/0238179 A1 | 9/2011 | Laurencin et al. |
| 2011/0257665 A1* | 10/2011 | Mortarino ............. A61F 2/0063 606/151 |
| 2012/0053689 A1* | 3/2012 | Martin .................. A61L 17/105 623/8 |
| 2013/0226204 A1 | 8/2013 | Kumar |
| 2014/0107797 A1 | 4/2014 | Sambusset |
| 2014/0222162 A1 | 8/2014 | Seedhom |
| 2014/0276993 A1* | 9/2014 | Reilly ...................... D04C 1/06 606/151 |
| 2014/0350675 A1 | 11/2014 | Hackney et al. |

FOREIGN PATENT DOCUMENTS

| | | |
|---|---|---|
| EP | 2206482 A1 | 7/2010 |
| FR | 2395012 A1 | 1/1979 |
| WO | 2007039159 A1 | 4/2007 |
| WO | 2007039160 A1 | 4/2007 |
| WO | 2010088699 A2 | 8/2010 |
| WO | 2012116319 A2 | 8/2012 |
| WO | 2012160070 A1 | 11/2012 |
| WO | 2013017836 A2 | 2/2013 |
| WO | 2016075650 A1 | 5/2016 |

\* cited by examiner

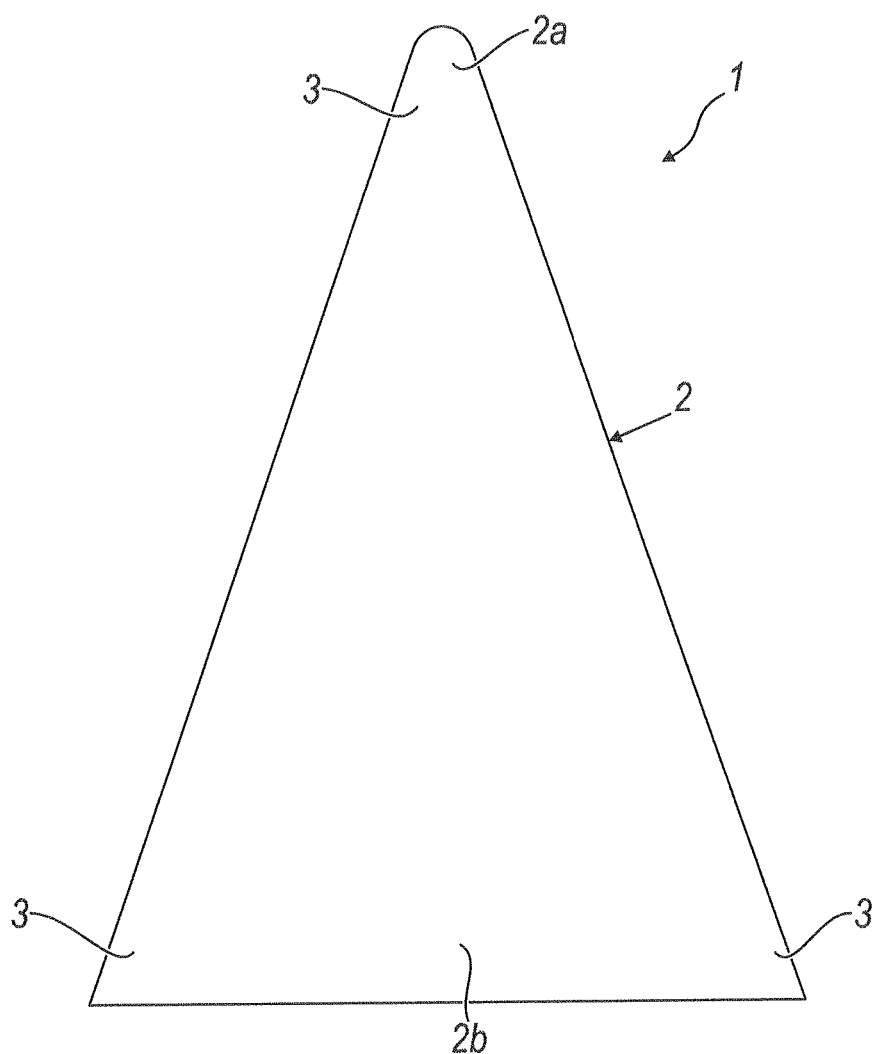

RESORBABLE DEVICE FOR RECONSTRUCTING ROTATOR CUFFS

CROSS-REFERENCE TO RELATED APPLICATIONS

This is a § 371 National Stage Application of International Application No. PCT/IB2015/058750 filed on Nov. 12, 2015, claiming the priority of Italian Patent Application No. MI2014A001959 filed on Nov. 13, 2014.

The object of the present invention is a device for the reconstruction of the rotator cuff.

The present invention has application in the cases of damage to one or more points of the muscle-tendon complex of the shoulder articulation, which commonly takes the name "rotator cuff."

As is known, devices exist which are fixed by means of suture to the damaged muscle-tendon tissue of the shoulder articulation (rotator cuff) in order to restore the functionality of the articulation.

Typically, these devices are made of non-resorbable and rigid materials. By way of example, the known devices are made of polyethylene terephthalate fibers, i.e. Dacron®. In this case, these temporarily restore the functionality of the damaged muscle-tendon tissue during the lesion healing phase. Subsequently, they remain in place and are not removed.

Disadvantageously, the materials used for making the known devices have a rigidity such to create a certain number of problems, above all in relation to their permanence in the articulation even after complete healing.

First of all, the excessive rigidity of the device can cause undesired separations of the device even after the convalescence phase, upon completed healing. In such unfavorable situation, it is necessary to once again subject the patient to a surgical operation in order to restore or remove the device.

In addition, the excessive rigidity of the device can cause limitations in the movement of the articulation of the patient even after the completion of the healing phase.

In any case, even without separations, the devices of known type, being permanent, can really irritate the patient in relation to their rigidity, among other things.

In this context, the technical task underlying the present invention is to propose a device for the reconstruction of the rotator cuff that overcomes the abovementioned drawback of the prior art.

In particular, the object of the present invention is to provide a device for the reconstruction of the rotator cuff that cannot cause any problem or limit following the healing phase.

The specified technical task and the specified object are substantially reached by a device for the reconstruction of the rotator cuff comprising the technical characteristics set forth in one or more of the enclosed claims.

Further characteristics and advantages of the present invention will be clearer from the exemplifying and therefore non-limiting description of a preferred but not exclusive embodiment of a device for the reconstruction of the rotator cuff, as illustrated in the enclosed drawings in which:

FIG. 1 is a schematic plan view of a device for the reconstruction of the rotator cuff.

With reference to the enclosed drawing, reference number 1 overall indicates a device for the reconstruction of the rotator cuff in accordance with the present invention.

The device 1 comprises a flat element 2, which has at least one first 2a and one second 2b end that are opposite each other.

The flat element 2, during use, is fixed by means of resorbable suture to the damaged muscle-tendon tissue of the rotator cuff.

The flat element 2 has a substantially wedge-shaped form. In other words, the flat element 2 has a substantially triangular form in plan view. In particular, the flat element 2 has the form of an isosceles triangle.

The vertex at the equivalent sides is rounded.

The vertex at the equivalent sides defines the first end 2a of the flat element 2.

The portion of flat element 2 at the base side opposite the vertex instead defines the second end 2b.

In accordance with the present invention, the flat element 2 of the device 1 is made of biodegradable and resorbable material. Advantageously, the flat element 2 of the device 1 is completely made of biodegradable and resorbable material.

Preferably, the flat element 2 of the device 1 is made of a PGA fiber fabric (polyglycolide or polyglycolic acid), preferably homopolymer. PGA is a highly biocompatible and resorbable polymer. In detail, the resorption time of PGA is approximately one month.

Advantageously, the use of PGA fibers in making the fabric of the flat element 2 allows the formation of muscle-tendon tissue during the device 1 resorption phase.

In other words, the flat element 2 is completely decomposed in the span of one month, without leaving any trace. Simultaneously, it facilitates the development of the muscle-tendon tissue.

In addition, once the device 1 is inserted, the fabric of the flat element 2 is soaked with blood and in particular with plasma, which allows the antibiotic drugs to be effective on the device itself.

The fabric of the flat element 2 can be obtained by weaving the PGA thread in various ways, giving rise to a knitted fabric, a woven fabric or a non-woven fabric.

Preferably, the fabric is a knitted fabric, still more preferably a warp knitted fabric.

In such case, the fabric has a rougher surface capable of assuming a net configuration with sufficiently small meshes.

In detail, its weft is such that its interstitial space is less than 200 µm, preferably around 160 µm, corresponding to an average area of the holes equal to approximately 0.02 mm$^2$. This ensures impermeability to urine, preventing leaks.

In addition, the fabric is preferably textured, in a manner so as to confer still greater surface roughness thereto.

Still merely by way of example, the fabric has a thickness substantially comprised between 0.3 mm and 0.6 mm, more preferably comprised between 0.4 mm and 0.53 mm, still more preferably being substantially 0.45 mm.

The device 1 has fixing areas 3 placed at the ends 2a, 2b of the flat element 2 for fixing, through resorbable suture, the flat element 2 to the damaged muscle-tendon tissue.

In particular, the fixing areas 3 are arranged at the vertices of the flat element 2.

The invention attains the aforesaid object.

Indeed, the resorption of the device during convalescence does not leave any residue in the articulation of the patient. Therefore, upon completed healing, the articulation remains completely free, without causing any irritation or impediment for the patient.

The invention claimed is:

1. A wedge-shaped biodegradable and resorbable device for a reconstruction of a rotator cuff, the device comprising:
   a flat element having two opposite ends adapted to be connected to at least one damaged tendon of the rotator cuff of a patient, wherein the flat element is entirely made of biodegradable and resorbable material, wherein the flat element is a triangular-shaped flat element having a rounded end at a vertex located at a first end of the two opposite ends and a base with two other vertices at a second end of the two opposite ends, wherein the flat element comprises fixing areas located at the two opposite ends of the flat element adapted to be employed for fixing, through resorbable suture, the flat element to the at least one damaged tendon, wherein the flat element is made of homopolymer PGA fiber fabric which continuously extends across the entire surface of the flat element such that there is an absence of a hole, wherein the homopolymer PGA fiber fabric is a warp knitted fabric having a thickness between 0.4 mm to 0.45 mm, and wherein the biodegradable and resorbable material is completely decomposed in a span of one month following implantation.

2. The device according to claim 1, further comprising resorbable suture, wherein the triangular-shaped flat element has an isosceles triangle form in plan view having the rounded end at the vertex located at a first end of the two opposite ends and a base with two other vertices defining acute angles with respective pointed ends at a second end of the two opposite ends, wherein the flat element comprises three said fixing areas attachable by suturing with respective resorbable suture, the three fixing areas located at the rounded vertex and two other vertices, respectively of the triangular-shaped flat element.

3. The device according to claim 1, wherein the flat element is made of fabric with a thread having a density between 50 and 200 denier.

4. The device according to claim 1, wherein the opposite ends of the triangular-shaped flat element include an upper end defined by the vertex of the triangular-shaped flat element and a lower end defined by the two vertices of the triangular-shaped flat element.

5. The device according to claim 4, wherein the flat element comprises three said fixing areas to allow the suturing, through resorbable suture, of the three fixing areas to the at least one damaged tendon, the three fixing areas located at the rounded vertex and two other vertices, respectively, of the triangular-shaped flat element.

6. The device according to claim 1, wherein the flat element is made of textured fabric.

7. The device according to claim 5, wherein the triangular-shaped flat element has an isosceles triangle form in plan view.

8. The device according to claim 7, wherein the isosceles triangle form has equal length sides extending from the vertex located at the first end.

9. The device according to claim 2, wherein the fabric has a weft defining interstitial space less than 200 μm with the weft having a thickness between 0.1 mm and 2 mm.

10. The device according to claim 1, wherein the wherein the fabric has a weft defining interstitial space of about 160 μm and having a weft thickness between 0.1 mm and 2 mm, and wherein the device comprises fixing areas located at the two opposite ends of the flat element adapted to be employed for fixing, through resorbable suture, the flat element to the at least one tendon.

11. The device according to claim 1, wherein the triangular-shaped flat element is a triangular-shaped element having an upper rounded vertex located at an upper end of the triangular-shaped element and two vertices located at a lower end of the triangular-shaped element.

12. The device according to claim 11, wherein the flat element is made of PGA fiber fabric having a thickness between 0.4 mm to 0.45 mm, wherein the triangular-shaped flat element has an isosceles triangle form in plan view, wherein the fabric has a weft defining interstitial space which is less than 200 μm with the weft having a thickness between 0.1 mm and 2 mm, and wherein the device comprises fixing areas located at the two opposite ends of the flat element adapted to be employed for fixing, through resorbable suture, the flat element to the at least one tendon.

13. The device according to claim 1, wherein the PGA fiber fabric is textured and made with a thread having a density between 50 and 200 denier.

14. The device according to claim 8, wherein the flat element comprises three said fixing areas to allow the suturing, through resorbable suture, of the three fixing areas to the at least one damaged tendon, the three fixing areas located at the rounded vertex and two other vertices, respectively, of the triangular-shaped flat element.

15. The device according to claim 1, wherein the flat element is made of the PGA fiber warp knitted fabric having the thickness between 0.4 mm to 0.45 mm, wherein the PGA fiber fabric has a weft defining interstitial space which is less than 200 μm with the weft having a thickness between 0.1 mm and 2 mm, wherein the PGA fiber fabric extends continuously across the entire surface of the flat element such that there is an absence of a hole, wherein the triangular-shaped flat element has an isosceles triangle form in plan view, wherein the triangular-shaped flat has an upper rounded vertex located at an upper end of the triangular-shaped element and two vertices located at a lower end of the triangular-shaped element, wherein the isosceles triangle form has equal length sides extending from the rounded vertex located at the upper end, and wherein the flat element comprises three fixing areas of said PGA fiber fabric for suturing, through resorbable suture, of the three fixing areas to the at least one damaged tendon, the three fixing are respectively located at the rounded vertex at the upper end of the flat element and two other vertices, respectively, of the triangular-shaped flat element at the opposite lower end of the flat element.

* * * * *